United States Patent
Elghazzawi

(10) Patent No.: US 10,993,626 B2
(45) Date of Patent: May 4, 2021

(54) RESCUE SCENE VIDEO TRANSMISSION

(71) Applicant: ZOLL Medical Corporation, Chelmsford, MA (US)

(72) Inventor: Ziad F Elghazzawi, Newton, MA (US)

(73) Assignee: ZOLL Medical Corporation, Chelmsford, MA (US)

( * ) Notice: Subject to any disclaimer, the term of this patent is extended or adjusted under 35 U.S.C. 154(b) by 492 days.

(21) Appl. No.: 15/485,277

(22) Filed: Apr. 12, 2017

(65) Prior Publication Data

US 2017/0281016 A1 Oct. 5, 2017

Related U.S. Application Data

(63) Continuation of application No. 13/538,031, filed on Jun. 29, 2012, now abandoned.

(51) Int. Cl.
| | |
|---|---|
| *A61B 5/0205* | (2006.01) |
| *A61N 1/39* | (2006.01) |
| *H04N 7/18* | (2006.01) |
| *H04W 4/90* | (2018.01) |
| *A61B 5/00* | (2006.01) |
| *H04W 4/70* | (2018.01) |

(52) U.S. Cl.
CPC .......... *A61B 5/0205* (2013.01); *A61N 1/3993* (2013.01); *H04N 7/181* (2013.01); *H04W 4/90* (2018.02); *A61B 5/0006* (2013.01); *A61B 5/0013* (2013.01); *A61B 5/0022* (2013.01); *H04W 4/70* (2018.02)

(58) Field of Classification Search
CPC ................ A61N 1/3993; A61N 1/3904; A61N 1/39044; A61N 1/39046
See application file for complete search history.

(56) References Cited

U.S. PATENT DOCUMENTS

| | | |
|---|---|---|
| 4,635,639 A | 1/1987 | Hakala |
| 5,038,800 A | 8/1991 | Oba |
| 5,434,611 A | 7/1995 | Tamura |
| 5,496,257 A | 3/1996 | Kelly |

(Continued)

FOREIGN PATENT DOCUMENTS

| | | |
|---|---|---|
| JP | 2002354141 A | 12/2002 |
| JP | 2010246712 | 11/2010 |

(Continued)

OTHER PUBLICATIONS

International Search Report and Written Opinion, PCT/US2013/043071, dated Aug. 26, 2013, 13 Pages.

(Continued)

*Primary Examiner* — Niketa I Patel
*Assistant Examiner* — Nathan A Baldwin
(74) *Attorney, Agent, or Firm* — Finch & Maloney PLLC

(57) ABSTRACT

A defibrillator or monitoring system may comprise a defibrillator, at least one video camera configured to acquire a video of a subject being treated by the defibrillator, a data collection unit configured to collect data associated with the subject, a communications unit configured to establish a communication channel between the defibrillator system and an emergency response center; and a processing unit configured to cause transmission to the emergency response center of at least one of the video of the subject and the data associated with the subject.

20 Claims, 5 Drawing Sheets

(56) References Cited

U.S. PATENT DOCUMENTS

| | | |
|---|---|---|
| 5,544,661 A | 8/1996 | Davis |
| 5,549,115 A | 8/1996 | Morgan |
| 5,549,659 A | 8/1996 | Johansen |
| 5,564,429 A | 10/1996 | Bornn |
| 5,593,426 A | 1/1997 | Morgan |
| 5,674,252 A | 10/1997 | Morgan |
| 5,680,864 A | 10/1997 | Morgan |
| 5,683,423 A | 11/1997 | Post |
| 5,701,904 A * | 12/1997 | Simmons ........... A61B 1/00108 348/42 |
| 5,724,025 A | 3/1998 | Tavori |
| 5,749,902 A | 5/1998 | Olson |
| 5,749,913 A | 5/1998 | Cole |
| 5,782,878 A | 7/1998 | Morgan |
| 5,787,155 A | 7/1998 | Luna |
| 5,836,993 A | 11/1998 | Cole |
| 5,862,803 A | 1/1999 | Besson |
| 5,891,046 A | 4/1999 | Cyrus |
| 5,891,049 A | 4/1999 | Cyrus |
| 5,899,866 A | 5/1999 | Cyrus |
| 5,921,938 A | 7/1999 | Aoyama |
| 5,951,485 A | 9/1999 | Cyrus |
| 5,999,493 A | 12/1999 | Olson |
| 6,014,257 A | 1/2000 | Furlani |
| 6,047,207 A | 4/2000 | MacDuff |
| 6,057,758 A | 5/2000 | Dempsey |
| 6,074,213 A | 6/2000 | Hon |
| 6,125,299 A | 9/2000 | Groenke |
| 6,141,584 A | 10/2000 | Rockwell |
| 6,150,951 A | 11/2000 | Olejniczak |
| 6,201,992 B1 | 3/2001 | Freeman |
| 6,221,010 B1 | 4/2001 | Lucas |
| 6,301,502 B1 | 10/2001 | Owen |
| 6,304,780 B1 | 10/2001 | Owen |
| 6,306,107 B1 | 10/2001 | Myklebust |
| 6,321,113 B1 | 11/2001 | Parker |
| 6,374,138 B1 | 4/2002 | Owen |
| 6,390,996 B1 | 5/2002 | Halperin |
| 6,398,744 B2 | 6/2002 | Bystrom |
| 6,405,083 B1 | 6/2002 | Rockwell |
| 6,427,083 B1 | 7/2002 | Owen |
| 6,438,417 B1 | 8/2002 | Rockwell |
| 6,459,933 B1 | 10/2002 | Lurie |
| 6,493,581 B2 | 12/2002 | Russell |
| 6,525,320 B1 | 2/2003 | Juni |
| 6,594,634 B1 | 7/2003 | Hampton |
| 6,597,948 B1 | 7/2003 | Rockwell |
| 6,668,192 B1 | 12/2003 | Parker |
| 6,691,952 B2 | 2/2004 | Keogh |
| 7,088,233 B2 | 8/2006 | Menard |
| 7,120,488 B2 | 10/2006 | Nova |
| 7,122,014 B2 | 10/2006 | Palazzolo |
| 7,138,902 B2 | 11/2006 | Menard |
| 7,231,258 B2 | 6/2007 | Moore |
| 7,277,752 B2 | 10/2007 | Matos |
| 7,769,465 B2 | 8/2010 | Matos |
| 8,170,887 B2 | 5/2012 | Rosenfeld |
| 8,175,895 B2 | 5/2012 | Rosenfeld |
| 8,185,623 B2 | 5/2012 | Lewis |
| 8,532,764 B2 | 9/2013 | Duke |
| 8,694,100 B2 | 4/2014 | Drew |
| 8,743,148 B2 | 6/2014 | Gegner |
| 8,823,490 B2 | 9/2014 | Libbus |
| 8,872,844 B2 | 10/2014 | Greiner |
| 9,531,837 B2 | 12/2016 | Brown |
| 2003/0025602 A1 | 2/2003 | Medema |
| 2003/0058097 A1 | 3/2003 | Saltzstein |
| 2003/0109904 A1 | 6/2003 | Silver |
| 2003/0212311 A1 | 11/2003 | Nova |
| 2003/0233129 A1 | 12/2003 | Matos |
| 2004/0015191 A1 | 1/2004 | Otman |
| 2004/0054760 A1 | 3/2004 | Ewing et al. |
| 2007/0060785 A1* | 3/2007 | Freeman ............... A61H 31/00 600/16 |
| 2007/0299473 A1* | 12/2007 | Matos ................. A61N 1/0476 607/5 |
| 2008/0097908 A1* | 4/2008 | Dicks ................. G06F 19/3418 705/50 |
| 2008/0146277 A1 | 6/2008 | Anglin |
| 2009/0054029 A1 | 2/2009 | Hogberg |
| 2009/0067586 A1 | 3/2009 | Fano |
| 2009/0284348 A1 | 11/2009 | Pfeffer |
| 2009/0295326 A1 | 12/2009 | Daynes |
| 2010/0160990 A1 | 6/2010 | Gotzy |
| 2011/0018998 A1* | 1/2011 | Guzik .................... H04N 21/21 348/143 |
| 2011/0092825 A1* | 4/2011 | Gopinathan .......... G16H 40/67 600/483 |
| 2011/0117529 A1 | 5/2011 | Barash |
| 2011/0295078 A1 | 12/2011 | Reid |

FOREIGN PATENT DOCUMENTS

| | | |
|---|---|---|
| WO | WO2002060529 | 8/2002 |
| WO | 2012065104 A2 | 5/2012 |
| WO | 2014003947 | 1/2014 |

OTHER PUBLICATIONS

JP Office Action received for JP Application No. 2015-520200, Office Action dated Aug. 29, 2019. 5 pages, including English translation.

Japanese Office Action for Application No. 2018-109052 with English computer translation, dated Jun. 4, 2019, 19 pages.

Extended European Search Report received for EP Application No. 19204252.1, dated Jan. 20, 2020. 13 pages.

* cited by examiner

RESCUE SCENE VIDEO TRANSMISSION

CROSS-REFERENCE TO RELATED APPLICATIONS

This application is a continuation under 35 U.S. C. § 120 of U.S. patent application Ser. No. 13/538,031, filed on Jun. 29, 2012. All subject matter set forth in the above referenced application is hereby incorporated by reference in its entirety into the present application as if fully set forth herein.

TECHNICAL FIELD

This disclosure relates to systems and techniques for rescue scene video communication, e.g., for a rescue scene in which a defibrillating device is used to treat a subject.

BACKGROUND

Sudden health problems such as sudden cardiac arrest and injuries caused by accidents kill thousands of people and cause permanent injury every year. Fast and competent care to resuscitate such subjects of these problems can be essential to positive outcomes in such situations. For example, it is said that the chance of surviving a sudden cardiac arrest falls by ten percent for every minute of delay in providing effective treatment.

Resuscitation treatments for patients suffering from cardiac arrest generally include clearing and opening the patient's airway, providing rescue breathing for the patient, and applying chest compressions to provide blood flow to the subject's heart, brain, and other vital organs. If the patient has a shockable heart rhythm (ventricular fibrillation or pulseless ventricular tachycardia), resuscitation also may include defibrillation therapy. Along with such action, an electrocardiogram (ECG) signal for the patient may be electronically captured, displayed, and monitored, so that rescuers can determine when the patient's heart has returned to normal or near-normal operation, and determine when the heart exhibits a shockable rhythm. About half of patients who suffer ventricular fibrillation (VF) have a recurrence of VF within minutes of successful VF conversion, which may then require reconversion. Patient odds of survival fall with repeated VF recurrence during resuscitation.

SUMMARY

Described herein are systems and techniques for transmitting and/or receiving video and/or audio communication between a rescue scene and an emergency response center. More particularly, one or more video cameras are included with a defibrillator, such as an automated external defibrillator (AED). When a subject (e.g., a victim of cardiac arrest) receives treatment from a caregiver with the assistance of the AED, the cameras acquire still and/or video images of the subject, the caregiver, and/or the rescue scene.

In some examples, a responder can select one or more cameras and/or microphones from which to receive video/audio transmission. For example, a still image acquired by each of the cameras is transmitted to the emergency response center, where a responder (e.g., a dispatcher) selects one or more of the images as representing a view for which he would like to receive a streaming video transmission. Video and/or audio from the camera(s)/microphones corresponding to the selected image(s) is transmitted in real-time to the emergency response center, enabling the responder to assess the situation at the rescue scene and/or provide guidance and instructions to the caregiver.

In some additional examples, if the bandwidth of the communication channel between the rescue scene and the emergency response center is limited, the transmission of the video and/or audio may be limited or stopped in order to allow preferential transmission of other information, such as subject monitoring data and/or audio conversations.

The systems and techniques described herein have a number of advantages. For instance, providing real-time video/audio of a rescue scene and/or a subject receiving treatment to a responder at an emergency response center enables the responder to assess the urgency of the situation at the rescue scene and react accordingly, e.g., by dispatching the appropriate first responders. In addition, by receiving the video and/or audio transmission, the responder may be able to guide a caregiver in the treatment of the subject and/or the operation of equipment (e.g., an automated external defibrillator (AED)) used to treat the subject. Furthermore, with multiple cameras and/or microphones associated with rescue equipment, there is a reasonable likelihood that at least one of the cameras and/or microphones will be positioned so as to capture the rescue scene, thus allowing the rescuer to focus on treatment of the subject without having to spend time setting up or adjusting a camera.

The details of one or more embodiments are set forth in the accompanying drawings and the description below. Other features and advantages will be apparent from the description and drawings, and from the claims.

DETAILED DESCRIPTION

Described herein are systems and techniques for video and/or audio bidirectional communication between a rescue scene and an emergency response center. More particularly, one or more video cameras and/or microphones are included with a defibrillator, such as an automated external defibrillator (AED) When a subject (e.g., a victim of cardiac arrest) receives treatment from a caregiver with the assistance of the AED, the cameras acquire still and/or video images of the subject, the caregiver, and/or the rescue scene. A still image acquired by each of the cameras is transmitted to the emergency response center, where a responder (e.g., a dispatcher) selects one or more of the images as representing a view for which he would like to receive a streaming video transmission. Video from the camera(s) corresponding to the selected image(s) and/or audio is communicated in real-time between emergency response center and the rescue scene, enabling the responder to assess the situation at the rescue scene and/or provide guidance and instructions to the caregiver. If the bandwidth of the communication channel between the rescue scene and the emergency response center is limited, the transmission of the video and/or audio may be limited or stopped in order to allow preferential transmission of other information, such as subject monitoring data and/or audio conversations.

Figure 1:
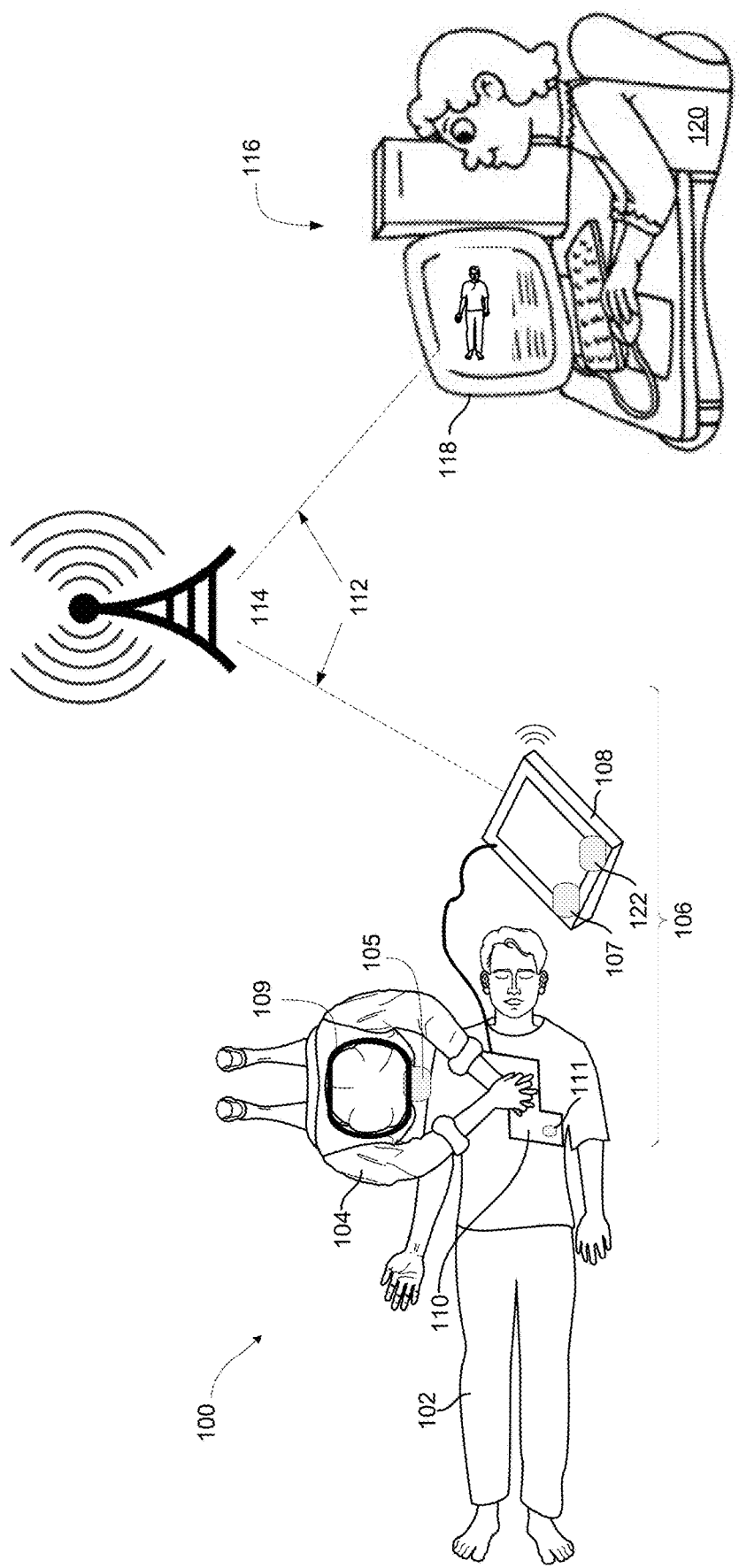
FIG. 1 is a schematic diagram of a rescue scene and an emergency response center.

Referring to FIG. 1, at a rescue scene 100, a caregiver 104 performs cardiopulmonary resuscitation (CPR) on a subject 102. An electronic defibrillating and/or monitoring system 106 including a defibrillator, such as an automated external defibrillator (AED) 108, a professional defibrillator, or another type of defibrillating apparatus, instructs the caregiver 104 in performing CPR and provides defibrillation as needed via external electrode pads 110. The subject may be, for instance, an individual who has apparently undergone sudden cardiac arrest. The caregiver may be, for instance, a civilian responder with limited or no training in lifesaving techniques; a first responder, such as an emergency medical technician (EMT), police officer, or firefighter; or a medical professional, such as a physician or nurse. The caregiver 104 may be acting alone or may be acting with assistance from one or more other caregivers, such as a partner EMT.

One or more video cameras, such as video cameras 105 and 107, are provided with the defibrillating system 106. The cameras 105, 107 are positioned to acquire still images and/or video images of various portions of the rescue scene 100, such as an image of a large part of the rescue scene 100, an image of the subject 102, an image of the caregiver's treatment of the subject, or another view. For instance, a camera (in this example, camera 105) may be mounted on a headpiece 109 or other wearable item that is to be worn by the caregiver 104, e.g., to provide a view of the caregiver's treatment of the subject. Another camera (in this example, camera 107) may be mounted on the AED 108, e.g., to provide a broad view of a large part of the rescue scene 100. Further, one or more cameras (e.g., camera 111) may be coupled or embedded with one or more electrodes such as electrode 110. Additional cameras may also be provided for positioning in other locations. For instance, a mobile (e.g., handheld) camera may be provided that can be held and operated by another caregiver or a bystander. A camera such as cameras 105 and 107 may include an embedded microphone configured to receive audio emanating from the rescue scene.

The defibrillating system 106 is connected via a communication channel 112 to an emergency response center 116, such as a 911 call center, a police dispatch, an ambulance dispatch, a fire department, or another emergency response center. In the illustrated example, the communication channel 112 is a long-range wireless communication channel (e.g., a 3G or 4G communication channel) supported by a wireless transmission tower 114, such as a cellular telephone tower. In other embodiments, the communication channel 112 may be a short-range wireless communication channel, such as a Bluetooth or WiFi connection, that is connected to a hardwired communication channel.

Images and/or video and audio from one or more of the cameras and/or microphones are communicated via the communication channel 112 between the emergency response center 116 and the rescue scene 100. The images and/or video are displayed on a display 118 (e.g., a computer monitor, television, mobile communication device, or other display) at the emergency response center 116, enabling a responder 120 (e.g., a dispatcher) to view the rescue scene 100 in real time. In some embodiments, the responder 120 may choose to receive video and/or audio from fewer than all of the cameras and/or microphones (e.g., from only one camera). For instance, the responder 120 may choose to view video from the camera that provides a desired view, such as a view of the subject 102 or a broad view of a large portion of the rescue scene 100.

In an embodiment, the defibrillating system 106 also monitors the subject 102 during treatment and collects real-time subject monitoring data. For instance, signals such as an ECG waveform, an SpO2 level, a blood pressure, a measure of cardiac output, or a measure of heart rate may be monitored. Alternatively or additionally, compression parameters, such as a sternal motion signal, a compression rate, a compression depth, or another measurement of compression, may be monitored. Some or all of these types of subject monitoring data may be transmitted to the emergency response center 116 via the communication channel 112. In some embodiments, the responder 120 may choose to view only some of the types of subject monitoring data.

In an embodiment, audio communication is also provided between the rescue scene 100 and the emergency response center 116. For instance, the defibrillating system 106 may include an audio device 122 including a microphone and speakers, which may be integrated into one or more of the cameras or may be a separate device (as shown in the illustrated example). Audio detected by the microphone in the audio device 122 (e.g., a conversion between the caregiver 104 and the subject 102 or between the caregiver 104 and another caregiver or bystander, or questions or comments from a caregiver to the responder 120) is transmitted to the emergency response center via the communication channel 112. Audio from the emergency response center 116 (e.g., questions or instructions by the responder 120) is transmitted to the defibrillating system 106 via the communication channel and played on the speakers in the audio device 122. For instance, while watching the streaming video, the responder 120 may be able to instruct the caregiver 104 in treatment of the subject 102, such as how to open a pouch containing electrodes, how to place electrodes and/or sensors on the subject, and how to perform CPR and/or other rescue operations. In addition, the responder 120 may be able to guide the caregiver in operation of the AED system 106, such as switching the language of the AED system, switching the AED system to or from adult or pediatric mode, and/or other system operations. In some instances, the responder 120 may be able to perform some AED system operations remotely on behalf of the caregiver.

Figure 2:
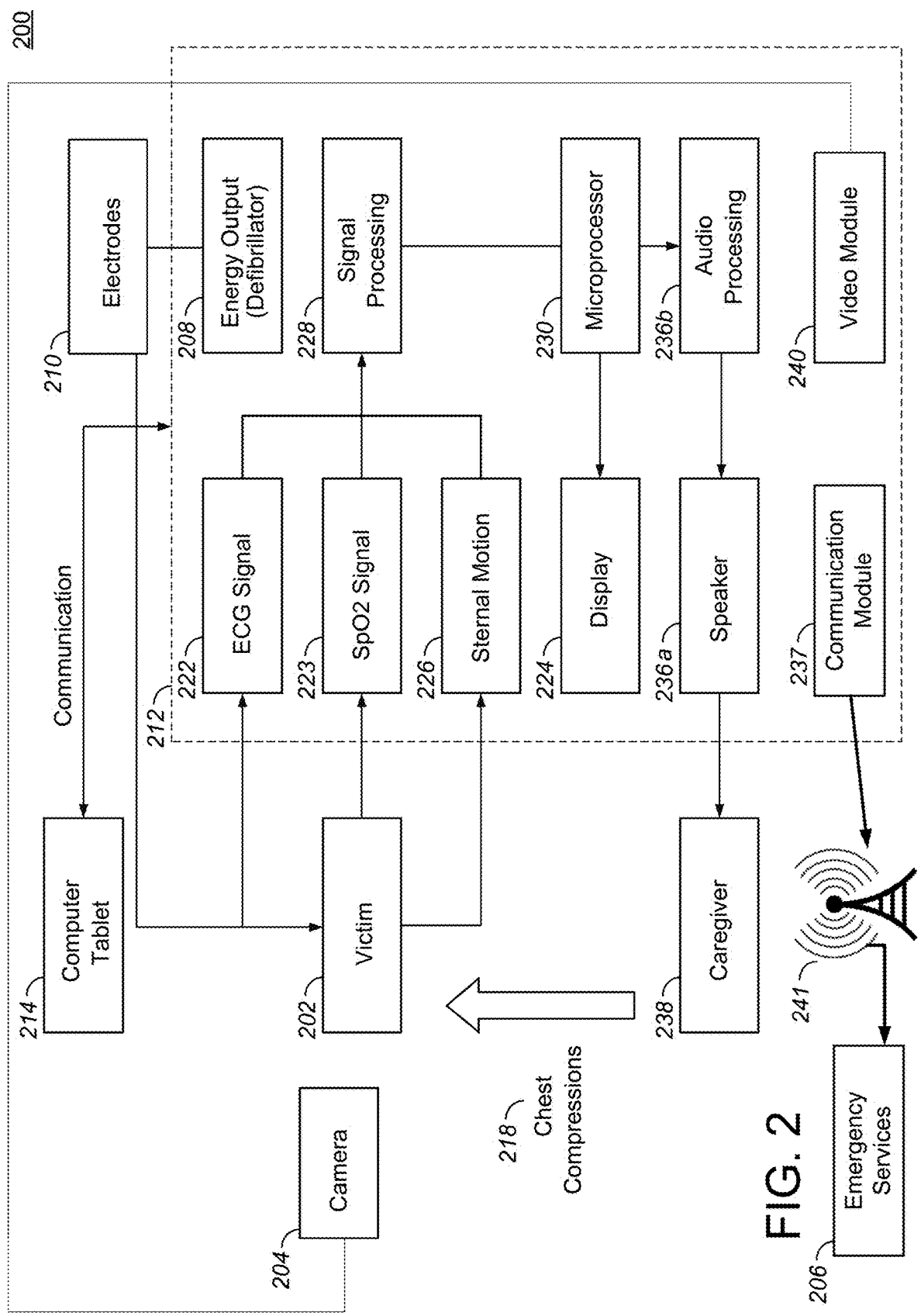
FIG. 2 is a block diagram of an example defibrillating system.

FIG. 2 is a block diagram of an example defibrillating system 200 for providing CPR and defibrillation assistance to a caregiver 238 administering care to a subject 202 and for communicating with an emergency response center 206. In general, the system 200 includes a number of medical devices that may be used to provide life-saving care to subject 202. The devices may be part of a single unit or multiple units, and may be used to monitor various real-time physical parameters of the subject 202, to communicate between the components and with remote systems such as central caregivers and emergency services, and to provide care to the subject 202 or provide instructions to caregivers, such as caregiver 238, in providing care to the subject 202.

The subject 202 is positioned to receive therapy from the caregiver 238 with the assistance of a Main Processing Unit (MPU) 212. For example, a set of defibrillator electrodes 210 has been applied to the subject's torso in a typical manner and is in wired connection to a portable external defibrillator 208 in the MPU 212. The defibrillator 208 may be, for example, a typical automated external defibrillator (AED), a professional defibrillator, or another similar type of defibrillating apparatus. A ventilation bag provides forced air into the subject's lungs to assist in rescue breathing for the subject. The defibrillator 208 and ventilation bag may be operated in familiar manners and in coordination by one or more caregivers. The ventilation bag may be fitted with various sensors and transmitters so as to collect data and to communicate electronically with the defibrillator 208. For example, a volumetric flow sensor provided with the ventilation bag may collect data about the volume of airflow to and from the subject, which data is transmitted to the defibrillator 208. The defibrillator 208 may relay these data, e.g., to the caregiver 238 and/or to the emergency response center 206; and/or may use the data to affect the manner in which defibrillation is provided to the subject 202.

A computer tablet 214 is provided in communication with the other devices of the system 200 and can be manipulated by the caregiver 238. The tablet 214 may serve as a general electronic command post for the caregiver 238 to receive information, e.g., about the subject 202, to communicate with other caregivers, and to provide input for controlling the operation of the components of the system 200. The tablet 214 may be provided with short range and/or long range wireless communication capabilities, such as Bluetooth, Wi-Fi, and/or cellular 3G or 4G capabilities. The tablet 214 may also be in data communication with sensors that sense real-time information about the subject 202, such as the subject's blood pressure, pulse, or other real-time subject monitoring data (discussed in more detail below). The caregiver 238 may input information into the tablet 214, such as information describing the condition of the subject 202 or other information that is to be recognized and recorded by the caregiver 238. The caregiver may also input information into tablet 214 so as to control one or more of the medical devices being used with the subject 202. For example, the caregiver may adjust the type, intensity, speed, or coordination of treatment that is provided to the subject 202.

The MPU 212 includes a communication module 237, which includes a transmitter and a receiver for providing a communication link between the MPU 212 and the emergency response center 206. The communication module 237 may include short range and/or long range wireless communication capabilities, such as Bluetooth, Wi-Fi, and/or cellular 3G or 4G capabilities. During operation, the communication module 237 sends a signal to a cellular tower 241, which in turn relays the signal to the emergency response center 206, thus establishing communication between the MPU 212 and the emergency response center 206. While shown in FIG. 2 as being included in the MPU 212, the communication module 237 could additionally or alternatively be included in the tablet 214.

Communication module 237 may enable the caregiver 238 to talk with a responder at the emergency response center 206, for instance to share information about the status of the subject 202, to request instructions, or to request assistance. Similarly, the responder may, for instance, provide instructions or support to the caregiver 238 or ask questions of the caregiver. In some cases, the communications module transmits some or all of the real-time patient monitoring data sensed by any of various sensors to the emergency response center 206 for viewing and/or analysis.

A video module 240 controls the operation of one or more cameras 204, which are positioned to acquire still and/or video images of the subject 202. For instance, one camera may be attached to the defibrillator 208 such that when the defibrillator is in operation, the camera is able to acquire an image of the subject. Another camera may be attached to a headpiece to be worn by the caregiver 238 so as to provide a close-up image of the subject 202 as the subject undergoes treatment. The videos acquired by one or more of the cameras may be sent to the emergency response center by the communications module. In some embodiments, a still image acquired by each of the cameras 204 is sent to the emergency response center so that a responder (e.g., a dispatcher, first responder, or other professional) can select the camera that presents a desired image. Once the responder selects a camera, video acquired by the selected camera is streamed to the emergency services center via the communications module.

In some cases, both subject data and video may be sent to the emergency response center. Depending on the communication link between the communication module and the emergency response center, there may not be sufficient bandwidth to support transmission of both subject data and video and/or audio. In this case, the video and/or transmission may be temporarily halted to allow for preferential transmission of the subject data to the emergency response center. Alternatively, the video may be transmitted at a lower frame rate than the frame rate at which the video was acquired by the camera (e.g., a ratio of the frame rate of the acquired video to the transmitted video can be at least 2:1, at least 3:1, or at least 4:1).

One or more sensors, such as sensors applied to the subject 202, provide input signals to MPU 212 that characterize the current real-time condition or physical parameters of the subject 202. The signals may be used by the MPU 212 to determine an appropriate treatment for the subject 202, such as a timing and/or force for chest compressions 218 delivered to the subject. For example, an ECG signal 222, obtained from leads connected to defibrillator 208, may represent the current and real-time ECG waveforms for the subject 202. An $SpO_2$ (oxygen saturation) signal 223 or another physiologically derived signal that is a direct or indirect measure of circulatory flow or perfusion, is obtained from a corresponding sensor. Other input signals may include physiological signals such as measures of cardiac output, measures of heart rate, blood pressure(s), ECG, oxygen saturation ($SpO_2$), heart sounds (e.g., phonocardiography), heart imaging (e.g., ultrasound), and/or impedance cardiography.

A signal processing unit 228 in the MPU 212 filters inputs, such as ECG inputs, for further analysis by a microprocessor 230. For example, the signal processing unit 228 may filter noise from input signals. In the case of ECG data, the signal processing unit 228 may filter artifacts created by chest compression motion 226 of the subject 202 in order to remove such artifacts. Such preparation of ECG signals may be termed SEE-THRU CPR®, and can be performed as discussed in U.S. Pat. No. 7,220,235, the contents of which are incorporated herein by reference in their entirety.

The microprocessor 230 receives input information associated with the real-time parameters of the subject 202, including ECG waveform data. The microprocessor 230 also performs analysis on such data to determine whether defibrillation is needed and/or to modify the feedback prompts provided by the display 224 and/or a speaker 236a controlled by an audio processing unit 236b.

Based on either retrospective data analysis of clinical datasets that include simultaneous recording of sternal motion signals and ECGs as well as patient outcome data, or of pre-clinical testing in animal models, a statistical model may have been developed that can predict the risk of fibrillation induction. The statistical model may in turn be used to determine an appropriate compression profile to be provided to a patient, and to be aligned in time with ECG data of the patient. The statistical model may be in the form of either a linear or non-linear regression equation, using such techniques as multiple logistic regression, for example.

The chest compression actions and/or other actions undertaken with respect to the subject 202 may be performed manually and may be prompted by various devices, including the MPU 212. Changes in compression profile may also be prompted via a manual process. For example, coordinated chest compression times and rates may be computed by the microprocessor 230 and verbally announced by the speaker 236a. For example, a metronome of beeping sounds may be played during CPR to indicate to the caregiver 238 when to press down on the subject's chest so as to avoid compressions or decompressions during a vulnerable period. Furthermore, the display 224 may provide coordinated visual feedback, such as a display of an ECG waveform, a graph of compression depth, or other similar data that may be helpful to the caregiver in providing care to the subject 202.

Figure 3:
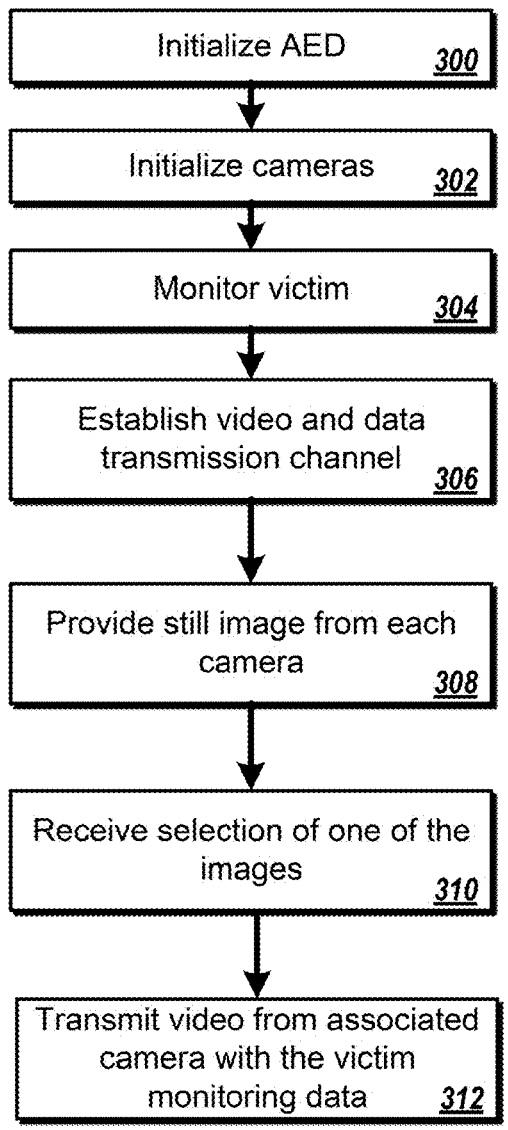
FIG. 3 is a flow chart of an example process for camera selection.

Referring to FIG. 3, in an example process for camera selection, an AED is associated with multiple video cameras. The cameras may be positioned to acquire still images and/or video images of various portions of the rescue scene, such as broad view of much of the rescue scene, an image of the subject, an image of the caregiver's treatment of the subject, or another view. For instance, a camera may be mounted on a headpiece or other wearable item that is to be worn by the caregiver, e.g., to provide a view of the caregiver's treatment of the subject. Another camera may be mounted on the AED, e.g., to provide a broad view of a large part of the rescue scene. Additional cameras may also be provided for positioning in other locations. For instance, a mobile (e.g., handheld) camera may be provided that can be held and operated by another caregiver or a bystander.

When a subject needs assistance (e.g., the subject appears to be experiencing sudden cardiac arrest), a caregiver initializes an AED (step 300). The cameras associated with the AED are also initialized (step 302). In some examples, the cameras are initialized automatically upon initialization of the AED. In other examples, one or more of the cameras are initialized manually, for example, when the caregiver turns on the camera or puts on a headpiece on which the camera is mounted. One or more of the cameras may be in a position to acquire a video image of the subject.

The subject is monitored (step 304) by one or more sensors during treatment, as discussed above, and real-time subject monitoring data is collected. For instance, signals such as an ECG waveform, an SpO$_2$ level, a blood pressure, a measure of cardiac output, or a measure of heart rate may be monitored. Alternatively or additionally, compression parameters may be monitored. Compression parameters may include, for instance, a sternal motion signal, compression velocity; compression depth; duty cycle; velocity of down stroke and/or upstroke; introthoracic pressure(s) during compressions; pleural pressure(s) during compressions; sternal position, velocity, and/or acceleration; chest wall or sternal strain or deformation; force applied to the chest; and/or pressure used to compress the chest by a mechanical chest compressor.

A video and data transmission channel is established (step 306) between the AED system and the emergency response center. For instance, the transmission channel may be a long-range wireless communication channel, such as a cellular 3G or 4G channel; or the transmission channel may be a short-range wireless communication channel, such as a Bluetooth or Wi-Fi connection, that is connected to a hard-wired communication channel.

A still image from each of the cameras is transmitted to the emergency response center (step 308) and displayed to a responder, e.g., on a display interface such as a computer monitor, television screen, mobile communications device, or other display interface. The responder is prompted to select one of the images. For instance, the responder may select the image that provides a view of the subject, a view of a large part of the rescue scene, a view of the caregiver's treatment of the subject, or another view.

The responder's selection is transmitted via the transmission channel and received by the AED system (step 310). Video from the camera associated with the selected image is transmitted to the emergency response center (step 312).

The video from the selected camera may be transmitted along with the subject monitoring data. In some embodiments, a listing of some or all of the available types of subject monitoring data is also presented to the responder on the display interface such that the responder may select one or more types of data for transmission. For instance, an ECG waveform, an SpO$_2$ level, a compression rate, and a compression depth may be available, from which the responder is prompted to select one or more for transmission. In some cases, the transmission of video and subject monitoring data may be controlled based on the available bandwidth of the communication channel, as described in greater detail below.

Figure 4:
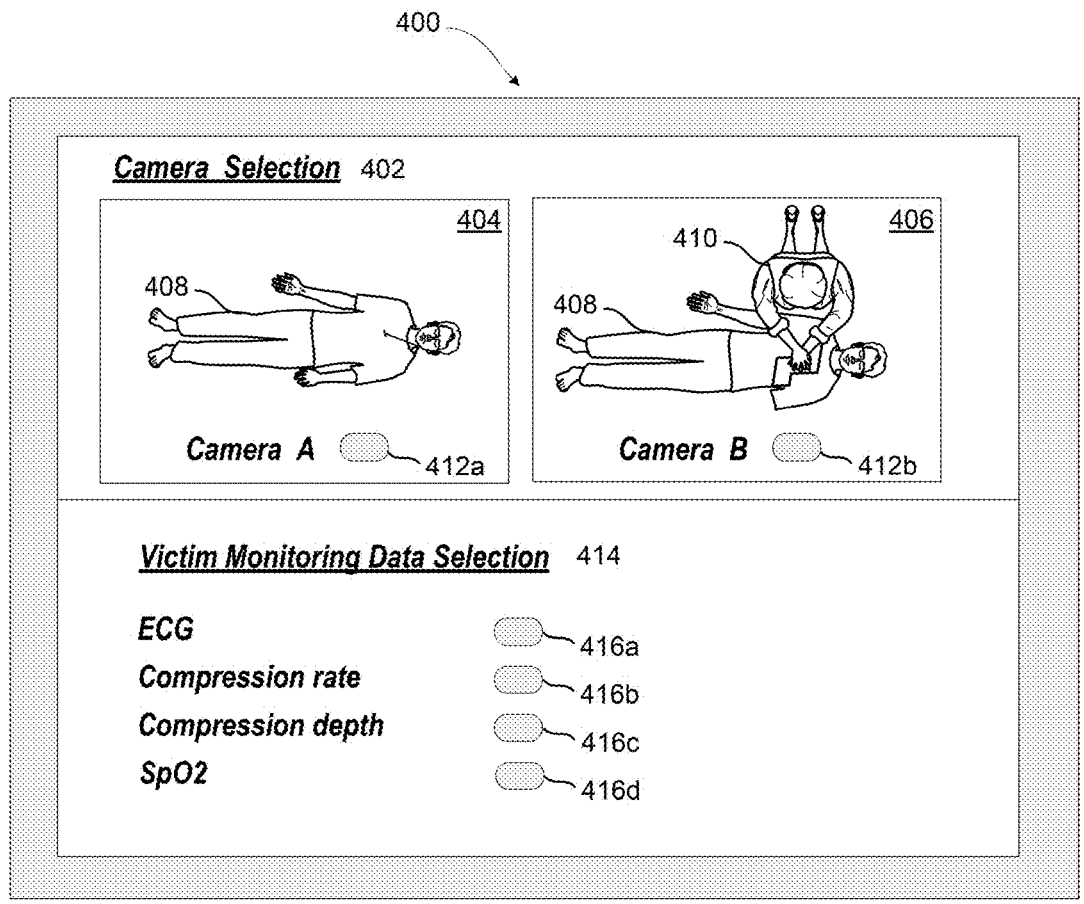
FIG. 4 is a schematic diagram of an example user interface.

Referring to FIG. 4, an example user interface 400 displayed on a display interface at the emergency response center allows a responder at the emergency response center to select an image corresponding to a desired camera view and which types of subject monitoring data to be transmitted.

In the illustrated example, a camera selection window 402 displays images 404 and 406 corresponding to cameras A and B, respectively. As can be seen from image 404, camera A is positioned to provide a view of a subject 408. As can be seen from image 406, camera B is positioned to provide a view of a caregiver 410 treating subject 408. The responder selects the image corresponding to the camera from which he would like to view video by selecting (e.g., clicking on) the appropriate selection button 412a, 412b.

The user interface 400 also includes a data selection window 414 that allows the responder to select one or more types of subject monitoring data to be transmitted. In the illustrated example, an ECG waveform, compression rate and depth data, and SpO$_2$ data are available for transmission. The responder selects one or more of the types of data that he would like to receive by selecting (e.g., clicking on) one or more of the appropriate selection buttons 416a, 416b, 416c, 416d.

The responder's image and data selections are transmitted back to the AED system at the rescue scene. Video from the camera corresponding to the selected image is streamed to the emergency response center. In addition, the selected type(s) of data are transmitted to the emergency response center. In some embodiments, the transmission of video and subject monitoring data may be controlled based on the available bandwidth of the communication channel, as discussed below.

In an alternative embodiment, video from all of the cameras is initially displayed on the user interface, and the responder is given the option to select one or more cameras for which to cease video transmission.

In another alternative embodiment, the user interface is provided at the rescue scene, e.g., on the tablet computer or another screen associated with the AED. The rescuer selects one or more cameras and/or types of subject monitoring data to be transmitted to the emergency response center.

Figure 5:
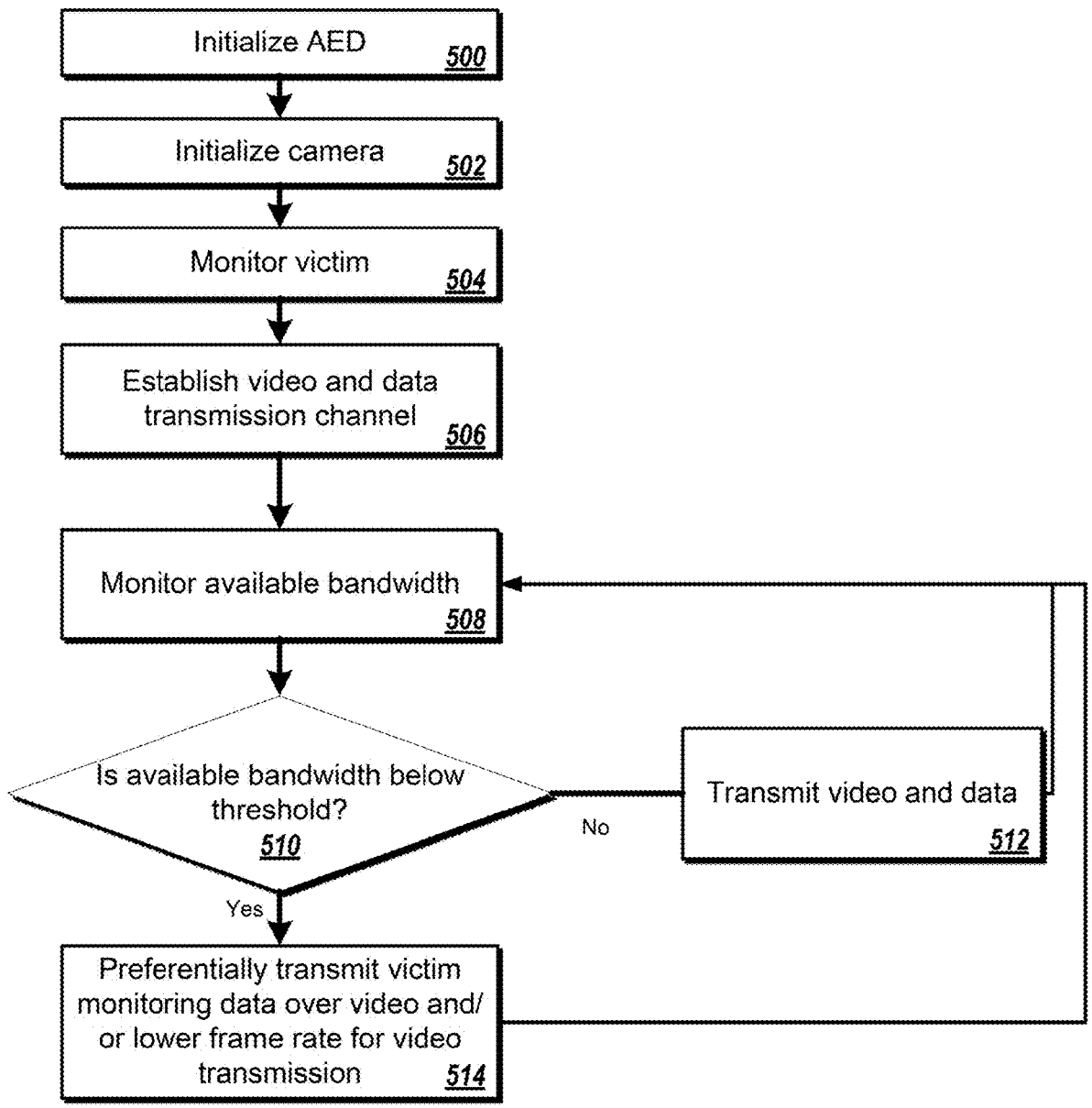
FIG. 5 is a flow chart of an example process for video and data transmission.

Referring to FIG. 5, in an example process, an AED provides the capability to control the transmission of subject monitoring data and/or video to the emergency response center based on the available bandwidth of the transmission channel.

When a subject needs assistance (e.g., the subject appears to be experiencing sudden cardiac arrest), a caregiver initializes an AED (step 500). One or more cameras associated with the AED are also initialized (step 502). In some examples, the cameras are initialized automatically upon initialization of the AED. In other examples, the cameras are initialized manually, for example, when the caregiver turns on a camera or puts on a headpiece on which a camera is mounted. The cameras may be in a position to acquire a video image of the subject. In some examples, one or more cameras previously selected by a responder at the emergency response center (e.g., as described above) are initialized.

The subject is monitored (step 504) by one or more sensors during treatment, as discussed above, and real-time subject monitoring data is collected. For instance, signals such as an ECG waveform, a $SpO_2$ level, a blood pressure, a measure of cardiac output, or a measure of heart rate may be monitored. Alternatively or additionally, compression parameters, such as a sternal motion signal or another measurement of compression, may be monitored.

A video and data transmission channel is established (step 506) between the AED system and the emergency response center. For instance, the transmission channel may be a long-range wireless communication channel, such as a cellular 3G or 4G channel; or the transmission channel may be a short-range wireless communication channel, such as a Bluetooth or Wi-Fi connection, that is connected to a hardwired communication channel.

The available bandwidth on the transmission channel is monitored (step 508) and a determination is made as to whether the available bandwidth is below a predetermined threshold (step 510). The threshold may be determined, for instance, based on an expected quantity of data to be sent via the transmission channel and/or a desired data transmission speed. In some examples, the threshold may be, e.g., 750 kbps, 1 Mbps, 1.5 Mbps, or another threshold.

If the available bandwidth is above the threshold, then the subject monitoring data and the video are both transmitted to the emergency response center via the transmission channel (step 512). If, however, the available bandwidth is below the threshold, the subject monitoring data may be preferentially transmitted to the emergency response center while the video is not transmitted (step 514). Alternatively, the subject monitoring data and the video may both be transmitted, but with the video at a lower frame rate than the frame rate at which the video was originally acquired (step 514). For instance, a ratio of the frame rate of the acquired video to the frame rate of the transmitted video may be at least 2:1, at least 3:1, or at least 4:1. In some embodiments, audio data may also be preferentially transmitted, e.g., when the available bandwidth is above a threshold for data-only transmission but below a threshold for full transmission of data, audio, and video.

The available bandwidth is monitored during the transmission of data and/or video to the emergency response center and adjustments are made as appropriate. For instance, if the bandwidth of the channel suddenly falls below the threshold, the video transmission may be stopped or the frame rate of the transmitted video may be reduced. Alternatively, if the bandwidth of the channel had been below the threshold but rises above the threshold, transmission of the video may be started.

The features described can be implemented in digital electronic circuitry, or in computer hardware, firmware, software, or in combinations of them. The apparatus can be implemented in a computer program product tangibly embodied in an information carrier, e.g., in a machine-readable storage device, for execution by a programmable processor; and method steps can be performed by a programmable processor executing a program of instructions to perform functions of the described implementations by operating on input data and generating output. The described features can be implemented advantageously in one or more computer programs that are executable on a programmable system including at least one programmable processor coupled to receive data and instructions from, and to transmit data and instructions to, a data storage system, at least one input device, and at least one output device. A computer program is a set of instructions that can be used, directly or indirectly, in a computer to perform a certain activity or bring about a certain result. A computer program can be written in any form of programming language, including compiled or interpreted languages, and it can be deployed in any form, including as a stand-alone program or as a module, component, subroutine, or other unit suitable for use in a computing environment.

Suitable processors for the execution of a program of instructions include, by way of example, both general and special purpose microprocessors, and the sole processor or one of multiple processors of any kind of computer. Generally, a processor will receive instructions and data from a read-only memory or a random access memory or both. The essential elements of a computer are a processor for executing instructions and one or more memories for storing instructions and data. Generally, a computer will also include, or be operatively coupled to communicate with, one or more mass storage devices for storing data files; such devices include magnetic disks, such as internal hard disks and removable disks; magneto-optical disks; and optical disks. Storage devices suitable for tangibly embodying computer program instructions and data include all forms of non-volatile memory, including by way of example semiconductor memory devices, such as EPROM, EEPROM, and flash memory devices; magnetic disks such as internal hard disks and removable disks; magneto-optical disks; and CD-ROM and DVD-ROM disks. The processor and the memory can be supplemented by, or incorporated in, ASICs (application-specific integrated circuits).

To provide for interaction with a user, the features can be implemented on a computer having a display device such as a CRT (cathode ray tube) or LCD (liquid crystal display) monitor for displaying information to the user and a keyboard and a pointing device such as a mouse or a trackball by which the user can provide input to the computer.

The features can be implemented in a computer system that includes a back-end component, such as a data server, or that includes a middleware component, such as an application server or an Internet server, or that includes a front-end component, such as a client computer having a graphical user interface or an Internet browser, or any combination of them. The components of the system can be connected by any form or medium of digital data communication such as a communication network. Examples of communication networks include, e.g., a LAN, a WAN, and the computers and networks forming the Internet.

The computer system can include clients and servers. A client and server are generally remote from each other and typically interact through a network, such as the described one. The relationship of client and server arises by virtue of computer programs running on the respective computers and having a client-server relationship to each other.

The computer system may include software for implementing an electronic patient care record, for example the ePCR software of ZOLL Data Systems (Broomfield Colo.). The software provides the ability to enter, store and transmit patient information as well as therapeutic interactions. The computer is often a so-called "tablet" computer system that has been ruggedized for pre-hospital use, but may also take the form of an IPHONE or IPAD. Data is preferably transmitted in real time between the portable "tablet" computer to an MPU 212, such as data that indicates the delivery of epinephrine to a subject. As epinephrine may increase risk of VF induction, notification of its delivery may be used by the MPU to adjust the compression parameters to further minimize risk of VF induction. Other separate treatments provided to the patient, or parameters of the patient condition sensed by the various sensors may also be provided to the tablet, and may factor into the rate, timing, force, or speed with which compressions and decompressions are performed on the patient.

A number of embodiments have been described. Nevertheless, it will be understood that various modifications may be made without departing from the spirit and scope of the invention. Accordingly, other embodiments are within the scope of the following claims.

What is claimed is:

1. A defibrillator system comprising:
   an external defibrillator;
   a chest compression sensor communicatively coupled to the external defibrillator and configured to generate signals indicative of chest compression parameter data for chest compressions provided to a medical rescue subject;
   one or more video cameras communicatively coupled to the external defibrillator and configured to acquire at least one video of the medical rescue subject;
   communications circuitry comprising a transmitter and a receiver together configured to establish a bi-directional communication channel between the defibrillator system and an emergency response center; and
   processing circuitry communicatively coupled to the communications circuitry, the processing circuitry comprising one or more processors configured to:
      receive the signals indicative of the chest compression parameter data from the chest compression sensor,
      receive the at least one video from the one or more video cameras,
      determine that at least one type of the chest compression parameter data is selected for transmission from amongst other types of chest compression parameter data,
      evaluate an available bandwidth of the bi-directional communication channel,
      in response to the available bandwidth being lower than a threshold bandwidth, transmit the signals indicative of the at least one type of chest compression parameter data to the emergency response center and halt transmission of the at least one video, and
      in response to the available bandwidth being greater than a threshold bandwidth, transmit the signals indicative of the at least one type of chest compression parameter data and the at least one video to the emergency response center.

2. The defibrillator system of claim 1, wherein one or more of the communications circuitry and the processing circuitry are disposed in the external defibrillator.

3. The defibrillator system of claim 1, comprising a mobile computing device communicatively coupled to the external defibrillator.

4. The defibrillator system of claim 3, wherein one or more of the communications circuitry and the processing circuitry are disposed in the mobile computing device.

5. The defibrillator system of claim 3, wherein the mobile computing device is one of a tablet computing device or a mobile communications device.

6. The defibrillator system of claim 1, wherein the threshold bandwidth is pre-determined based on an expected quantity of subject monitoring data.

7. The defibrillator system of claim 6, wherein the one or more processors are configured to preferentially transmit the subject monitoring data if the available bandwidth of the bi-directional communication channel is below the threshold bandwidth.

8. The defibrillator system of claim 1, comprising one or more medical sensors communicatively coupled to the one or more processors and configured to send medical sensor data to the one or more processors.

9. The defibrillator system of claim 8, wherein the one or more processors are configured to: receive the medical sensor data, send, via the transmitter, to the emergency response center, a list of types of medical sensor data available in the received medical sensor data; receive, via the receiver, from the emergency response center, selected types of medical sensor data from the list of the types of medical sensor data available in the received medical sensor data; and control transmission, via the transmitter, to the emergency response center, of the selected types of medical sensor data based on the available bandwidth of the bi-directional communication channel.

10. The defibrillator system of claim 9, wherein the types of medical sensor data comprise one or more of electrocardiogram (ECG) data, oxygen saturation data, cardiac output data, heart rate data, heart sound data, heart imaging data, and impedance cardiography data.

11. The defibrillator system of claim 1, comprising a microphone configured to detect audio at a site of the medical rescue subject and comprising speakers configured to audibly provide audio information transmitted from the emergency response center and received at the receiver.

12. The defibrillator system of claim 11, wherein the one or more processors are configured to, based on the available bandwidth of the bi-directional communication channel, control transmission, via the transmitter, of the detected audio to the emergency response center to preferentially allow reception the audio information transmitted from the emergency response center.

13. The defibrillator system of claim 11, wherein the audio information comprises cardiopulmonary resuscitation (CPR) instructions.

14. The defibrillator system of claim 11, wherein the audio information comprises one or more of instructions as to how to open electrode packaging, instructions as to how to place electrodes on the medical rescue subject, and instructions as to how to place one or more medical sensors on the medical rescue subject and the one or more processors are configured to control the speakers to audibly provide the one or more of the instructions as to how to open electrode packaging, the instructions as to how to place electrodes on the medical rescue subject, and the instructions as to how to place the one or more medical sensors on the medical rescue subject.

15. The defibrillator system of claim 11, comprising a mobile computing device communicatively coupled to the external defibrillator wherein the microphone and the speakers are disposed in the mobile computing device.

16. The defibrillator system of claim 11, wherein the microphone and the speakers are disposed in the external defibrillator.

17. The defibrillator system of claim 1, comprising a ventilation device communicatively coupled to the external defibrillator wherein the one or more processors are configured to control transmission of ventilation data, received from the ventilation device, to the emergency response center based on the available bandwidth of the bi-directional communication channel.

18. The defibrillator system of claim 1, wherein the communications circuitry is configured to provide one or more of short range wireless communications and long range wireless communications.

19. The defibrillator system of claim 1, wherein the chest compression parameter data comprises data for one or more of sternal motion, compression velocity, compression depth, duty cycle, downstroke velocity, upstroke velocity, intrathoracic pressure, pleural pressure, sternal position, sternal velocity, sternal acceleration, sternal strain, sternal deformation, compression force, and compression pressure.

20. The defibrillator system of claim 1, comprising a mechanical chest compression device wherein the chest compression parameter data is associated with chest compressions delivered to the medical rescue subject by the mechanical chest compression device.

\* \* \* \* \*